United States Patent
Agrawal et al.

(10) Patent No.: US 6,489,464 B1
(45) Date of Patent: *Dec. 3, 2002

(54) BRANCHED OLIGONUCLEOTIDES AS PATHOGEN-INHIBITORY AGENTS

(75) Inventors: Sudhir Agrawal, Shrewsbury, MA (US); Susan Meschwitz, Saunderstown, RI (US)

(73) Assignee: Hybridon, Inc., Cambridge, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 9 days.

(21) Appl. No.: 08/664,786

(22) Filed: Jun. 17, 1996

Related U.S. Application Data

(63) Continuation of application No. 08/252,494, filed on Jun. 1, 1994, now abandoned.

(51) Int. Cl.[7] .............................................. C07H 21/04
(52) U.S. Cl. ...................... 536/24.5; 536/23.1
(58) Field of Search ......................... 514/44; 536/23.72, 536/23.1, 24.1, 25.3, 24.5; 435/91.1

(56) References Cited

U.S. PATENT DOCUMENTS

| | | | | |
|---|---|---|---|---|
| 4,806,403 A | | 2/1989 | Goodchild et al. ............ | 435/5 |
| 5,194,428 A | * | 3/1993 | Agrawal et al. .............. | 514/44 |
| 5,215,899 A | * | 6/1993 | Dattagupta ..................... | 435/6 |
| 5,399,676 A | | 3/1995 | Froehler ..................... | 536/23.1 |
| 5,543,507 A | * | 8/1996 | Cook et al. ................. | 536/23.1 |

FOREIGN PATENT DOCUMENTS

| | | |
|---|---|---|
| EP | 0552767 | 7/1993 |
| WO | WO8908146 | 9/1989 |
| WO | WO9106626 | 5/1991 |
| WO | WO9203051 | 3/1992 |
| WO | WO9205284 | 4/1992 |
| WO | WO9313740 | 7/1993 |
| WO | WO9401551 | 1/1994 |

OTHER PUBLICATIONS

Gura, Antisense has growing pains, Science, vol. 270, pp. 575–577, Oct. 1995.*
Graham et al. 1990, Proc. Natl. Acad. Sci. USA, 87:5817–5821.*
Agrawal et al., *Trends in Biotech.* 10, 152 (1992).
Rapaport et al., *Proc. Natl. Acad. Sci. USA* 89, 8577–8580 (1992).
Sarin et al., *Proc. Natl. Acad. Sci. USA* 85, 7448–7451 (1988).
Temsamani et al., *Ann. N.Y. Acad. Sci.* 660, 318–320 (1992).
Tang et al., *Nucleic Acids Res.* 21, 2729 (1993).
Koga et al., *J. Org. Chem.,* 56 3757–3759 (1991).
Agrawal et al., *Proc. Natl. Acad. Sci. USA* 85, 7079–7083 (1988).
Seliger et al., *Nucleosides & Nucleotides* 10, 469–477 (1991).
Ortiago et al., *Antisense Res. & Dev.* 2, 129–146 (1992).
Horne and Dervan, *J. Am. Chem. Soc.* 112, 2435–2437 (1990).
Luebke and Dervan, *Nucleic Acids Res.* 20, 3005–3009 (1992).
van de Sande et al., *Science* 241, 551–557 (1988).
Lisziewicz et al., *Proc. Natl. Acad. Sci. USA* 89, 11209–11213 (1992).
Uhlmann and Peyman, *Chemical Reviews* 90, 543 (1990).
Schneider and Banner, *Tetrahedron Letts.* 31, 335 (1990).
Kumar and Poonian, *J. Org. Chem.* 49, 4905–4912 (1984).
Smith et al., *J. Org. Chem. Soc.* 84, 430 (1962).
Sinha et al., *Nucleic Acids Res.* 12, 4539–4557 (1984).
Damha et al., *Nucleic Acids Res.* 18, 3813–3821 (1990).

* cited by examiner

*Primary Examiner*—Andrew Wang
(74) *Attorney, Agent, or Firm*—Hale and Dorr LLP

(57) ABSTRACT

Novel antisense oligonucleotides are disclosed. The present oligonucleotides have increased resistance to nuclease attack and manifest increased efficacy in combating pathogenic infections. The present oligonucleotides comprise two or more identical or different sequences, each complementary to a nucleic acid sequence of a pathogen that is essential to the pathogen's metabolism and/or reproduction. The sequences may be complementary to the same or different target nucleic acid sequence within a single pathogen, to target sequences on different strains of the same pathogen, or to target sequences on different pathogens. In the preferred embodiment, the sequences are coupled via a 3'–3' linkage, which greatly reduces 3' nucleolytic degradation.

8 Claims, 10 Drawing Sheets

X = O or S

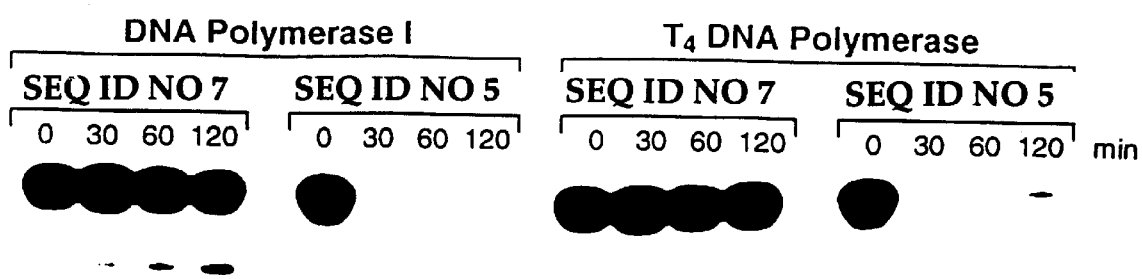
FIG. 5

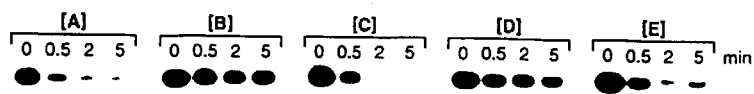

[A] 5' CUUACAGGAGAGAGAUGGGUGCGAGCGCCAUUUUCAGAAUUGGGUGUUGCAU 3'
       TCCTCTCTCTACCCACGCTC

[B] 5' CUUACAGGAGAGAGAUGGGUGCGAGCGCCAUUUUCAGAAUUGGGUGUUGCAU 3'
                                      GGTAAAAGTCTTAACCCACA

[C] 5' CUUACAGGAGAGAGAUGGGUGCGAGCGCCAUUUUCAGAAUUGGGUGUUGCAU 3'
       3' ⎛TCCTCTCTCTACCCACGCTC  ⎛GGTAAAAGTCTTAACCCACA
       3' ⎝GGTAAAAGTCTTAACCCACA  ⎝TCCTCTCTCTACCCACGCTC

[D] 5' CUUACAGGAGAGAGAUGGGUGCGAGCGCCAUUUUCAGAAUUGGGUGUUGCAU 3'
                          3' ⎛GGTAAAAGTCTTAACCCACA
                          3' ⎝TCCTCTCTCTACCCACGCTC
                          5'  AGGAGAGAGATGGGTGCGAG

[E] 5' CUUACAGGAGAGAGAUGGGUGCGAGCGCCAUUUUCAGAAUUGGGUGUUGCAU 3'
       3' ⎛TCCTCTCTCTACCCACGCTC
       3' ⎝GGTAAAAGTCTTAACCCACA
       5'  CCATTTTCAGAATTGGGTGT

FIG. 8

SEQUENCE LISTING (1) GENERAL INFORMATION:

(iii) NUMBER OF SEQUENCES: 19

(2) INFORMATION FOR SEQ ID NO:1:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (iii) HYPOTHETICAL: NO (iv) ANTI-SENSE: YES (xi) SEQUENCE DESCRIPTION: SEQ ID NO:1:

CTCGCACCCA TCTCTCTCCT                                                    20

(2) INFORMATION FOR SEQ ID NO:2:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (iii) HYPOTHETICAL: NO (iv) ANTI-SENSE: YES (ix) FEATURE:
      (A) NAME/KEY: misc_feature
      (B) LOCATION: 1..20
      (D) OTHER INFORMATION: /note= "All phosphorothioate
          internucleotide linkages"

(xi) SEQUENCE DESCRIPTION: SEQ ID NO:2:

CTCGCACCCA TCTCTCTCCT                                                    20

(2) INFORMATION FOR SEQ ID NO:3:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (iii) HYPOTHETICAL: NO (iv) ANTI-SENSE: YES (xi) SEQUENCE DESCRIPTION: SEQ ID NO:3:

ACACCCAATT CTGAAAATGG                                                    20

(2) INFORMATION FOR SEQ ID NO:4:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (iii) HYPOTHETICAL: NO (iv) ANTI-SENSE: YES (ix) FEATURE:
      (A) NAME/KEY: misc_feature (B) LOCATION: 1..20
            (D) OTHER INFORMATION: /note= "All phosphorothioate
                internucleotide linkages"

(xi) SEQUENCE DESCRIPTION: SEQ ID NO:4:

ACACCCAATT CTGAAAATGG                                                      20

(2) INFORMATION FOR SEQ ID NO:5:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (iii) HYPOTHETICAL: NO (iv) ANTI-SENSE: YES (xi) SEQUENCE DESCRIPTION: SEQ ID NO:5:

CTCGCACCCA TCTCTCTCCT TTACACCCAA TTCTGAAAAT GG                              42

(2) INFORMATION FOR SEQ ID NO:6:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (iii) HYPOTHETICAL: YES (iv) ANTI-SENSE: YES (ix) FEATURE:
        (A) NAME/KEY: misc_feature
        (B) LOCATION: 1..42
        (D) OTHER INFORMATION: /note= "All phosphorothioate
            internucleotide linkages"

(xi) SEQUENCE DESCRIPTION: SEQ ID NO:6:

CTCGCACCCA TCTCTCTCCT TTACACCCAA TTCTGAAAAT GG                              42

(2) INFORMATION FOR SEQ ID NO:7:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (iii) HYPOTHETICAL: NO (iv) ANTI-SENSE: YES (ix) FEATURE:
        (A) NAME/KEY: misc_feature
        (B) LOCATION: 21..22
        (D) OTHER INFORMATION: /note= "3'-3' internucleotide linkage"

(ix) FEATURE:
        (A) NAME/KEY: misc_feature
        (B) LOCATION: 22..42
        (D) OTHER INFORMATION: /note= "These bases are listed 3'->5'
            left to right."

(xi) SEQUENCE DESCRIPTION: SEQ ID NO:7:

CTCGCACCCA TCTCTCTCCT TTGGTAAAA GTCTTAACCCA CA                              42

(2) INFORMATION FOR SEQ ID NO:8:

```
     (i) SEQUENCE CHARACTERISTICS:
         (A) LENGTH: 42 base pairs
         (B) TYPE: nucleic acid
         (C) STRANDEDNESS: single
         (D) TOPOLOGY: linear (iii) HYPOTHETICAL: NO (iv) ANTI-SENSE: YES (ix) FEATURE:
         (A) NAME/KEY: misc_feature
         (B) LOCATION: 21..22
         (D) OTHER INFORMATION: /note= "3'-3' internucleotide linkage"

(ix) FEATURE:
         (A) NAME/KEY: misc_feature
         (B) LOCATION: 22..42
         (D) OTHER INFORMATION: /note= "These bases are listed 3'->5'
             left to right."

(ix) FEATURE:
         (A) NAME/KEY: misc_feature
         (B) LOCATION: 1..42
         (D) OTHER INFORMATION: /note= "All phosphorothioate
             internucleotide linkages"

(xi) SEQUENCE DESCRIPTION: SEQ ID NO:8:

CTCGCACCCA TCTCTCTCCT TTGGTAAAAA GTCTTAACCCA CA                        42

(2) INFORMATION FOR SEQ ID NO:9:

(i) SEQUENCE CHARACTERISTICS:
         (A) LENGTH: 42 base pairs
         (B) TYPE: nucleic acid
         (C) STRANDEDNESS: single
         (D) TOPOLOGY: linear (iii) HYPOTHETICAL: NO (iv) ANTI-SENSE: YES (ix) FEATURE:
         (A) NAME/KEY: misc_feature
         (B) LOCATION: 21..22
         (D) OTHER INFORMATION: /note= "3'-3' internucleotide linkage"

(ix) FEATURE:
         (A) NAME/KEY: misc_feature
         (B) LOCATION: 22..42
         (D) OTHER INFORMATION: /note= "These bases are listed 3'->5'
             left to right."

(ix) FEATURE:
         (A) NAME/KEY: misc_feature
         (B) LOCATION: 23..42
         (D) OTHER INFORMATION: /note= "This region was synthesized by
             random incorporation of the bases A, T, C, and G""

(xi) SEQUENCE DESCRIPTION: SEQ ID NO:9:

CTCGCACCC ATCTCTCTCCT TTNNNNNNNN NNNNNNNNNNNN                          42

(2) INFORMATION FOR SEQ ID NO:10:

(i) SEQUENCE CHARACTERISTICS:
         (A) LENGTH: 42 base pairs
         (B) TYPE: nucleic acid
         (C) STRANDEDNESS: single
         (D) TOPOLOGY: linear (iii) HYPOTHETICAL: NO (iv) ANTI-SENSE: YES (ix) FEATURE:
```

(A) NAME/KEY: misc_feature
            (B) LOCATION: 21..22
            (D) OTHER INFORMATION: /note= "3'-3' internucleotide linkage"

(ix) FEATURE:
            (A) NAME/KEY: misc_feature
            (B) LOCATION: 22..42
            (D) OTHER INFORMATION: /note= "These bases are listed 3'->5'
                  left to right."

(ix) FEATURE:
            (A) NAME/KEY: misc_feature
            (B) LOCATION: 23..42
            (D) OTHER INFORMATION: /note= "This region was synthesized by
                  random incorporation of the bases A, T, C, and G""

(ix) FEATURE:
            (A) NAME/KEY: misc_feature
            (B) LOCATION: 1..42
            (D) OTHER INFORMATION: /note= "All phosphorothioate
                  internucleotide linkages"

(xi) SEQUENCE DESCRIPTION: SEQ ID NO:10:

CTCGCACCC ATCTCTCTCCT TTNNNNNNNN NNNNNNNNNN NN                          42

(2) INFORMATION FOR SEQ ID NO:11:

(i) SEQUENCE CHARACTERISTICS:
            (A) LENGTH: 42 base pairs
            (B) TYPE: nucleic acid
            (C) STRANDEDNESS: single
            (D) TOPOLOGY: linear (iii) HYPOTHETICAL: NO (iv) ANTI-SENSE: YES (ix) FEATURE:
            (A) NAME/KEY: misc_feature
            (B) LOCATION: 21..22
            (D) OTHER INFORMATION: /note= "3'-3' internucleotide linkage"

(ix) FEATURE:
            (A) NAME/KEY: misc_feature
            (B) LOCATION: 22..42
            (D) OTHER INFORMATION: /note= "These bases are listed 3'->5'
                  left to right."

(ix) FEATURE:
            (A) NAME/KEY: misc_feature
            (B) LOCATION: 23..42
            (D) OTHER INFORMATION: /note= "This region was synthesized by
                  random incorporation of the bases A, T, C, and G""

(xi) SEQUENCE DESCRIPTION: SEQ ID NO:11:

ACACCCAAT TCTGAAAATGG TTNNNNNNNN NNNNNNNNNN NN                          42

(2) INFORMATION FOR SEQ ID NO:12:

(i) SEQUENCE CHARACTERISTICS:
            (A) LENGTH: 42 base pairs
            (B) TYPE: nucleic acid
            (C) STRANDEDNESS: single
            (D) TOPOLOGY: linear (iii) HYPOTHETICAL: NO (iv) ANTI-SENSE: YES (ix) FEATURE:
            (A) NAME/KEY: misc_feature
            (B) LOCATION: 21..22
            (D) OTHER INFORMATION: /note= "3'-3' internucleotide linkage"

(ix) FEATURE:

(A) NAME/KEY: misc_feature
         (B) LOCATION: 21..42
         (D) OTHER INFORMATION: /note= "These bases are listed 3'->5'
             left to right."

(ix) FEATURE:
         (A) NAME/KEY: misc_feature
         (B) LOCATION: 23..42
         (D) OTHER INFORMATION: /note= "This region was synthesized by
             random incorporation of the bases A, T, C, and G""

(ix) FEATURE:
         (A) NAME/KEY: misc_feature
         (B) LOCATION: 1..42
         (D) OTHER INFORMATION: /note= "All phosphorothioate
             internucleotide linkages"

(xi) SEQUENCE DESCRIPTION: SEQ ID NO:12:

ACACCCAAT TCTGAAAATGG TTNNNNNNNN NNNNNNNNNN NN                              42

(2) INFORMATION FOR SEQ ID NO:13:

(i) SEQUENCE CHARACTERISTICS:
         (A) LENGTH: 42 base pairs
         (B) TYPE: nucleic acid
         (C) STRANDEDNESS: single
         (D) TOPOLOGY: linear (iii) HYPOTHETICAL: NO (iv) ANTI-SENSE: YES (ix) FEATURE:
         (A) NAME/KEY: misc_feature
         (B) LOCATION: 21..22
         (D) OTHER INFORMATION: /note= "3'-3' internucleotide linkage"

(ix) FEATURE:
         (A) NAME/KEY: misc_feature
         (B) LOCATION: 22..42
         (D) OTHER INFORMATION: /note= "These bases are listed 3'->5'
             left to right."

(ix) FEATURE:
         (A) NAME/KEY: misc_feature
         (B) LOCATION: 1..20
         (D) OTHER INFORMATION: /note= "This region was synthesized by
             random incorporation of the bases A, T, C, and G"

(ix) FEATURE:
         (A) NAME/KEY: misc_feature
         (B) LOCATION: 22..42
         (D) OTHER INFORMATION: /note= "This region was synthesized by
             random incorporation of the bases A, T, C, and G"

(xi) SEQUENCE DESCRIPTION: SEQ ID NO:13:

NNNNNNNNNN NNNNNNNNNN TTNNNNNNNN NNNNNNNNNN NN                              42

(2) INFORMATION FOR SEQ ID NO:14:

(i) SEQUENCE CHARACTERISTICS:
         (A) LENGTH: 42 base pairs
         (B) TYPE: nucleic acid
         (C) STRANDEDNESS: single
         (D) TOPOLOGY: linear (iii) HYPOTHETICAL: NO (iv) ANTI-SENSE: YES (ix) FEATURE:
         (A) NAME/KEY: misc_feature
         (B) LOCATION: 21..22
         (D) OTHER INFORMATION: /note= "3'-3' internucleotide linkage"

```
    (ix) FEATURE:
         (A) NAME/KEY: misc_feature
         (B) LOCATION: 22..42
         (D) OTHER INFORMATION: /note= "These bases are listed 3'->5'
             left to right."

(ix) FEATURE:
         (A) NAME/KEY: misc_feature
         (B) LOCATION: 1..20
         (D) OTHER INFORMATION: /note= "This region was synthesized by
             random incorporation of the bases A, T, C, and G"

(ix) FEATURE:
         (A) NAME/KEY: misc_feature
         (B) LOCATION: 22..42
         (D) OTHER INFORMATION: /note= "This region was synthesized by
             random incorporation of the bases A, T, C, and G"

(ix) FEATURE:
         (A) NAME/KEY: misc_feature
         (B) LOCATION: 1..42
         (D) OTHER INFORMATION: /note= "All phosphorothioate
             internucleotide linkages"

(xi) SEQUENCE DESCRIPTION: SEQ ID NO:14:

NNNNNNNNNN NNNNNNNNNN TTNNNNNNNN NNNNNNNNNN NN                        42

(2) INFORMATION FOR SEQ ID NO:15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (iii) HYPOTHETICAL: NO (iv) ANTI-SENSE: YES (ix) FEATURE:
         (A) NAME/KEY: misc_feature
         (B) LOCATION: 1..20
         (D) OTHER INFORMATION: /note= "This sequence was synthesized
             by random incorporation of the bases A, T, C, and G"

(xi) SEQUENCE DESCRIPTION: SEQ ID NO:15:

NNNNNNNNNN NNNNNNNNNN                                                 20

(2) INFORMATION FOR SEQ ID NO:16:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (iii) HYPOTHETICAL: NO (iv) ANTI-SENSE: YES (ix) FEATURE:
         (A) NAME/KEY: misc_feature
         (B) LOCATION: 1..20
         (D) OTHER INFORMATION: /note= "This sequence was synthesized
             by random incorporation of the bases A, T, C, and G"

(ix) FEATURE:
         (A) NAME/KEY: misc_feature
         (B) LOCATION: 1..20
         (D) OTHER INFORMATION: /note= "All phosphorothioate
             internucleotide linkages"

(xi) SEQUENCE DESCRIPTION: SEQ ID NO:16:

NNNNNNNNNN NNNNNNNNNN                                                 20
```

(2) INFORMATION FOR SEQ ID NO:17:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (iii) HYPOTHETICAL: NO (iv) ANTI-SENSE: YES (xi) SEQUENCE DESCRIPTION: SEQ ID NO:17:

CUUACAGGAG AGAGAUGGGU GCGAGCGCCA UUUUCAGAAU UGGGUGUUGC AU    52

(2) INFORMATION FOR SEQ ID NO:18:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (iii) HYPOTHETICAL: NO (iv) ANTI-SENSE: YES (xi) SEQUENCE DESCRIPTION: SEQ ID NO:18:

AGGAGAGAGA TGGGTGCGAG    20

(2) INFORMATION FOR SEQ ID NO:19:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (iii) HYPOTHETICAL: NO (iv) ANTI-SENSE: YES (xi) SEQUENCE DESCRIPTION: SEQ ID NO:19:

CCATTTTCAG AATTGGGTGT    20

BRANCHED OLIGONUCLEOTIDES AS PATHOGEN-INHIBITORY AGENTS

This application is a file-wrapper continuation of application Ser. No 08/252,494, filed Jun. 1, 1994 now abandoned.

BACKGROUND OF THE INVENTION

1. Field of the Invention

The invention relates to synthetic oligonucleotides that have an inhibitory effect upon pathogens. More particularly, the invention relates to anti-pathogen synthetic oligonucleotides having superior inhibitory properties relative to known oligonucleotides.

2. Summary of the Related Art

The use of synthetic oligonucleotides as anti-infecting agents has recently developed into a promising field. Agrawal, Trends in Biotechnology 10:152–158 (1992), reviews the development of antisense oligonucleotides as antiviral agents. Synthetic oligonucleotides now show considerable promise not only as antiviral agents, but as inhibitors of other pathogens as well. Rapaport et al., Proc. Natl. Acad. Sci. USA 89:8577–8580 (1992), discloses antimalarial activities of oligonucleotide phosphorothioates against Plasmodium falciparum.

Due to the great promise of synthetic oligonucleotides as anti-infective agents, considerable interest has developed in improving the pharmacological properties of such compounds. Many such efforts have involved introducing modified internucleoside linkages into oligonucleotides, thereby providing increased resistance to nucleolytic degradation and improving biostability. Agrawal et al., Proc. Natl. Acad. Sci. USA 85:7079:7083 (1988), teaches inhibition of human immunodeficiency virus (HIV) propagation by oligodeoxynucleotide phosphorothioates and phosphoramidites. Sarin et al., Proc. Natl. Acad. Sci. USA 85:7448–7451 (1988), discloses inhibition of HIV by oligodeoxynucleotide methylphosphonates. Padmapriya and Agrawal, Bioorganic & Medicinal Chemistry Letters 3:761–764 (1993), discloses oligonucleotides having novel methylphosphonothioate internucleoside linkages.

Goodchild and Zamecnik (U.S. Pat. No. 4,806,463) disclose antisense oligonucleotides that inhibit HTLV-III replication and protein expression. These oligonucleotides are targeted to highly conserved regions in the HTLV-III genome. Among the sites targeted are: a) the $rRNA^{lys}$ primer binding site, b) regions of the HTLV-III genome vicinal in the 5' direction to the $rRNA^{lys}$ primer binding site, c) the $tRNA^{lys}$ primer binding site and regions of the HTLV-III genome vicinal in the 5'direction to the $tRNA^{lys}$ primer binding site, d) the mRNA donor splice sites, e) the mRNA acceptor splice sites, f) the initiator codon for the gag gene, g) the initiator condon for the env gene, h) the initiator codon for the tat gene, i) the initiator codon for the sor gene, j) the initiator codon for the 3' orf gene, k) the cap nucleotide of the HTLV-III genome, l) the art gene or portions thereof, m) and the region of the HTLV-III genome encoding a frameshift.

Other modifications, not necessarily involving solely the use of modified phosphodiester internucleotide linkage, have included the introduction of chemical blocking structures at the 3' end of oligonucleotides. Temsamani et al., Annals of the New York Academy of Sciences 660:318–320 (1992), teaches that 3'-capped oligonucleotide phosphorothioates have superior in vivo pharmacokinetics and bioability relative to uncapped oligonucleotide phosphorothioates. Tang et al., Nucleic Acids Res. 21:2729 (1993), teaches that oligonucleotides having 3' terminal hairpin structures demonstrate superior biostability. Koga et al., J. Org. Chem. 56:3757–3759 (1991), reports improved nuclease resistance for alternating $\alpha,\beta$-oligothymidylates having alternating (3' to 3') and (5' to 5') internucleotide phosplhodiester linkages. Seliger et al., Nucleosides & Nucleotides 10:469–477 (1991), and Ortigao et al., Antisense Research & Development 2:129–146 (1992), disclose improved resistance to nucleolytic degradation for oligodeoxynucleotides having single terminal 3' to 3' and 5' to 5' linkage inversions.

Methods for synthesizing oligonucleotides having at least one 3' to 3' internucleoside linkage can involve the use of modified nucleoside monomers that allow 5' to 3' synthesis or the use of linkers from which dual 3' to 5' synthesis of oligonucleotides having 3' to 3' and 5' to 5' linkages using commercially available 5' phosphoramidite nucleoside monomers. CLONETECHniques (April 1993) discloses synthesis of oligonucleotides having a single 3' to 3' internucleoside linkage using a commercially available branched linker. Horne and Dervan, J. Am. Chem. Soc. 112:2435–2437 (1990); Luebke and Dervan, Nucleic Acids Res. 20:3005–3009 (1992); and van de Sande et al., Science 241:551–557 (1988), disclose similar synthesis of oligonucleotides having a single 3' to 3' linkage for the purpose of studying alternate strand triple helix formation or parallel stranded DNA.

Certain potential problems for effective use of synthetic oligonucleotides as anti-infective therapeutics arise, however, from the nature of the target, rather than the oiligonucleotide, and are thus not addressed by improving the biostability of the oligonucleotide. One such problem is the potential for an infective agent to escape oligonucleotide-mediated therapy by mutation of the target sequence, thereby reducing the ability of the oligonucleotide to interact with the target sequence. For example, Lisziewicz et al., Proc. Natl. Acad. Sci. USA 89:11209–11213 (1992) teaches that a splice acceptor site antisense oligonucleotide initially suppressed HIV in infected MOLT-3 cells, but that after 25 days, viral breakthrough of the suppression was observed. This report suggests that combined or sequential treatment with oligonucleotides complementary to distinct targets may be useful in avoiding viral breakthrough.

There remains a need for additional means of providing biostability to synthetic oligonucleotides that inhibit pathogens. There also remains a need for new ways to avoid mutation-derived breakthrough of pathogens. Ideally, an oligonucleotide should be developed that overcomes both of these problems.

BRIEF SUMMARY OF THE INVENTION

The invention relates to synthetic oligonucleotides that have an inhibitory effect upon pathogens. The invention provides anti-pathogen synthetic oligonucleotides that have superior inhibitory properties, relative to known oligonucleotides. The superior inhibitory properties of oligonucleotides according to the invention are the result of the primary structural feature of such oligonucleotides, which is the linking together of two or more oligonucleotide sequences that are complementary to one or more essential gene of one or more pathogen.

In a first aspect, the invention provides oligonucleotides having two or more identical oligonucleotide sequences linked together, wherein each oligonucleotide sequence is complementary to the same target sequence of a pathogen. The target sequence is the sequence of a portion of a gene or regulatory sequence that is essential for the propagation of the pathogen. According to this aspect of the invention, the identical oligonucleotide sequences may be linked together in a 5' to 3' configuration or in a 3' to 3' configuration. In this latter configuration, the oligonucleotide is highly resistant to nucleolytic degradation.

In a second aspect, the invention provides oligonucleotides having two or more different oligonucleotide sequences linked together, wherein each oligonucleotide sequence is complementary to a different target sequence of the same pathogen. The different oligonucleotide sequences may be complementary to different portions of the same gene or regulatory sequence or they may be complementary to different genes and/or regulatory sequences. Oligonucleotides according to this aspect of the invention provide improved resistance to mutation-induced pathogen escape from the inhibitory effect of the oligonucleotide. The different oligonucleotide sequences may be linked together in 5' to 3' or 3' to 3' configurations, with the latter configuration providing greatly increased resistance to nucleolytic degradation.

In a third aspect, the invention provides oligonucleotides having two or more different oligonucleotide sequences linked together, wherein one or more oligonucleotide sequence is complementary to a target sequence from one pathogen and one or more oligonucleotide sequence is complementary to a gene or regulatory sequence from another pathogen. Oligonucleotides according to this aspect of the invention provide combined treatment for infections involving two different pathogens. The different oligonucleotide sequences may be linked together in 5' to 3' or 3' to 3' configurations, with the latter configuration providing greatly increased resistance to nucleolytic degradation.

In a fourth aspect, the invention provides oligonucleotides having two or more different oligonucleotide sequences linked together, wherein one or more oligonucleotide sequence is complementary to a gene or regulatory sequence from one strain of a pathogen and one or more oligonucleotide sequence is complementary to a gene or regulatory sequence from another strain of the same pathogen. Oligonucleotides according to this aspect of the invention provide the advantage of being effective at inhibiting two or more strains of the pathogen, thus allowing the oligonucleotide to be used as an inhibitory agent even before the particular strain of the pathogen is known.

Those skilled in the art will appreciate that combinations of the various aspects of the invention may be employed within a single oligonucleotide to provide an oligonucleotide having superior characteristics for the treatment of particular disease conditions. They will also recognize that if the identical or different oligonucleotide sequences of the first three aspects of the invention have a 3' terminal ribonucleotide, then the identical or different oligonucleotides can be linked by 5' to 3', 5' to 2', 2' to 3', 3' to 2', or 3' to 3' linkages.

It is an object of the invention to provide anti-pathogen oligonucleotides that reduce or eliminate mutation-induced pathogen escape from the inhibitory effect of the oligonucleotide. It is a further object of the invention to provide anti-pathogen oligonucleotides that can inhibit more than one pathogen simultaneously, particularly where such pathogens commonly coinfect host organisms in nature.

The foregoing merely summarizes certain aspects of the present invention and is not intended, nor should it be construed, to limit the invention in any way.

All patents and publications cited herein are hereby incorporated by reference in their entirety.

BRIEF DESCRIPTION OF THE DRAWINGS

FIG. 5 shows the results of digestion of 5'-$^{32}$P end labelled oligonucleotides 3 (PO) and 4 (PO) by the 3'-exonucleolytic activity of E. coli DNA polymerase (which also contains some 5'-exonucleolytic activity) and $T_4$ DNA polymerase.

FIG. 8 shows the results of RNase H cleavage of a oligonucleotia duplexes (SEQ ID NOS: 1,3,5,7 and 17). The 52-mer in [A]–[E] is SEQ ID NO: 17. The oligonucleotide antisense to it in [A] is SEQ ID NO: 2 and in [B] is SEQ ID NO: 4. In [C] both antisense oligonucleotides are SEQ ID NO: 8. In [D] the 3'-3' linked oligonucleotide is SEQ ID NO: 8 and the 20-mer oligonucleotide is SEQ ID NO: 18. In [E] the 3'-3' linked oligonucleotide is SEQ ID NO: 8 and the 20-mer oligonucleotide is SEQ ID NO: 19.

DETAILED DESCRIPTION OF THE PREFERRED EMBODIMENTS

Figure 1:
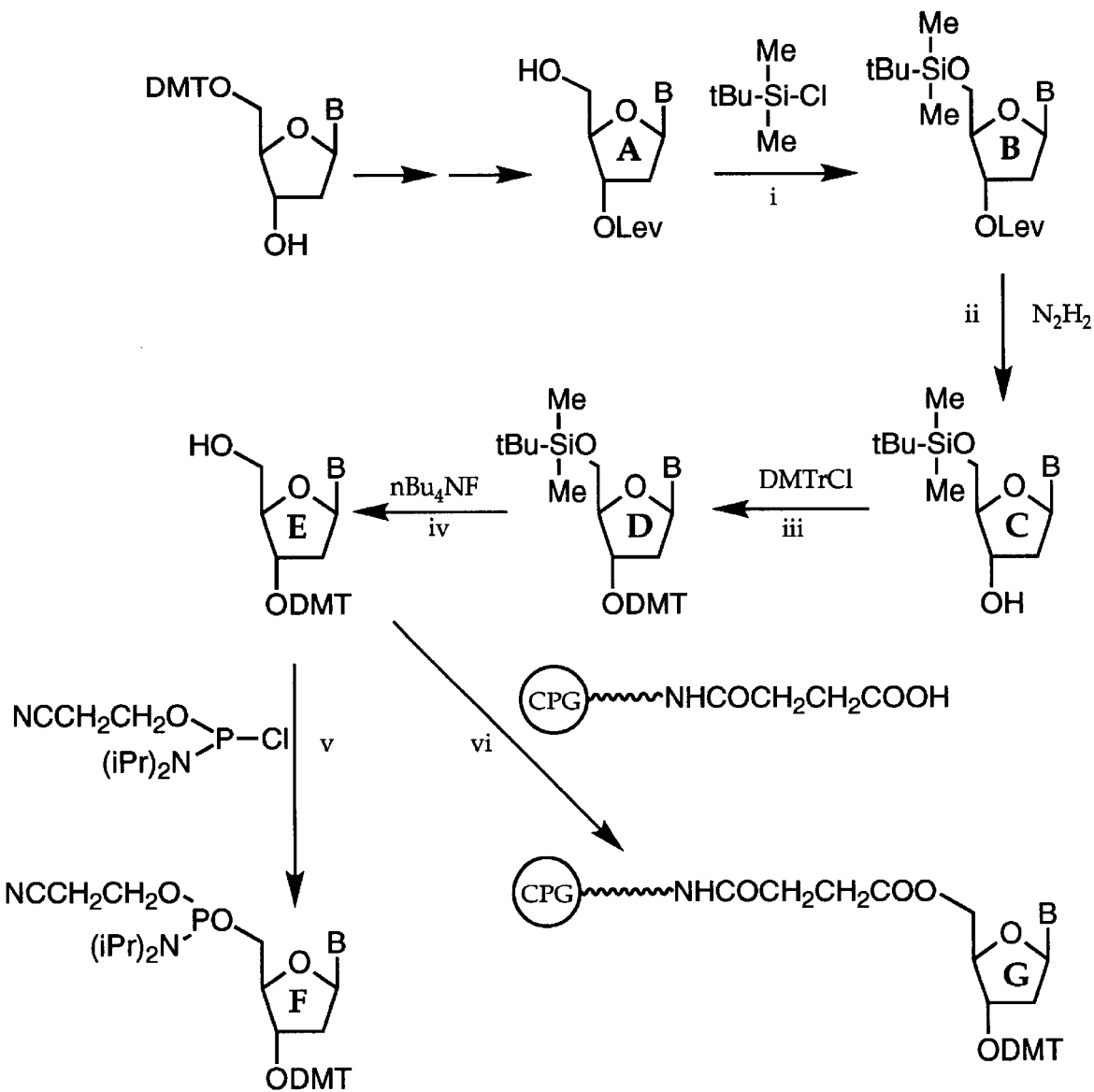
FIG. 1 shows the general synthesis scheme for 5'-phosphoramidites and nucleosides 5'-linked to CPG.

This invention relates to synthetic oligonucleotides that have an inhibitory effect upon pathogens. The invention provides anti-pathogen synthetic oligonucleotides that have superior inhibitory properties against pathogens. The superior inhibitory properties of various embodiments of oligonucleotides according to the invention arise from the oligonucleotides linked to each other via a 5' to 3', 5' to 2', or preferably a 3' to 3', 3' to 2', or 2' to 3' interoligonucleotide linkage. When the oligonucleotides are linked together via a 5' to 3' linkage, the sequences of the oligonucleotides are sequences that are noncontiguous in any naturally occurring nucleic acid.

In a first aspect, the invention provides oligonucleotides having two or more identical oligonucleotide sequences linked together. In oligonucleotides according to this aspect of the invention, the identical oligonucleotide sequences are both complementary to the same target nucleotide sequence of a pathogen. The target sequence is the sequence of a portion of a gene or regulatory sequence that is essential for the disease causing effect of the pathogen. Oligonucleotides according to this aspect of the invention have a greater inhibitory effect upon the disease causing affect of the pathogen than conventional oligonucleotides.

In a second aspect, the invention provides oligonucleotides having two or more different oligonucleotide sequences linked together. In oligonucleotides according to this aspect of the invention, the different oligonucleotide sequences are complementary to target nucleotide sequences of the same pathogen. These different target sequences may be different sites within the same gene or regulatory sequence, or they may be different genes and/or regulatory sequences. Such oligonucleotides offer the advantage of being able to overcome mutation-induced escape by the pathogen from the inhibitory effect of the oligonucleotide. When an anti-pathogen oligonucleotide is used that is complementary to only a single target nucleotide sequence, the pathogen can potentially escape the inhibitory effect of the oligonucleotide through mutation of the target nucleotide sequence such that the oligonucleotide is not capable of hybridizing with the target nucleotide sequence. The likelihood of such escape is greatly reduced when an oligonucleotide is used that has oligonucleotide sequence complementary to two different target sequences, because the frequency of simultaneous multiple mutations is the product of the frequencies of the individual mutations. Oligonucleotides according to this aspect of the invention provide several advantages over simultaneous or sequential administration of oligonucleotides that are complementary to different target nucleotide sequences. First, they are simpler to use, because only the single compound needs to be synthesized and administered. This single compound advantage also extends to easier quality control and to simpler validation for regulatory purposes when the oligonucleotides are intended for human or veterinary use.

In a third aspect, the invention again provides oligonucleotides having two or more different oligonucleotide sequences linked together. In oligonucleotides according to this aspect of the invention, however, the different oligonucleotide sequences are complementary to target nucleotide sequences from different pathogens. These target nucleotide sequences are portions of genes or regulatory sequences that are essential to the disease causing effect of each pathogen. Oligonucleotides according to this aspect of the invention provide the advantage of allowing one to synthesize and administer a single compound that can inhibit the disease causing effect of two different pathogens that might be expected to co-affect the host, as is commonly seen with human immunodeficiency virus (HIV) and either cytomegalovirus, influenza, Pneumocystis carnii, or Mycobacterium tuberculosis. In tissue culture studies, a further example is any virus to be studied and contaminating mycoplasma that can complicate the results of such a study.

In a fourth aspect, the invention again provides oligonucleotides having two or more different oligonucleotide sequences. In oligonucleotides according to this aspect of the invention, however, the different oligonucleotide sequences are complementary to target nucleotide sequences of different strains or alleles of the same pathogen. These target nucleic acid sequences may be the same or different portions of genes or regulatory sequences that are essential to the disease causing effect of the pathogen. Oligonucleotides according to this aspect of the invention provide the advantage of allowing one to synthesize and administer a single compound that can inhibit the disease causing effect of a pathogenic species, without having to know which strain or allele of the pathogen is affecting the host.

The following nomenclature applies to oligonucleotides according to each aspect of the invention. The term "oligonucleotide sequences" includes oligonucleotides that may optionally have additional ribonucleotide, 2'-substituted ribonucleotide, and/or deoxyribonucleotide monomers, any of which are connected together via 5' to 3' linkages, which may include any of the internucleotide linkages known in the art. Preferably, such oligonucleotides may optionally contain phosphodiester, phosphotriester, phosphoramidate, siloxane, carbonate, carboxymethylester, acetamidate, carbamate, thioether, bridged phosphoramidate, bridged methylene phosphonate, bridged phosphorothioate and/or sulfone internucleotide linkages. The synthesis of oligonucleotides containing any of these internucleotide linkages is well known to those skilled in the art, as is illustrated, for example, by articles of Uhlmann and Peyman, Chemical Reviews 90:543–584 (1990) and Schneider and Banner, Tetrahedron Lett. 31:335 (1990). Preferably, oligonucleotide sequences of oligonucleotides according to the invention should contain from about 6 to about 100 monomers in total, most preferably from about 8 to about 50 monomers. Such modified oligonucleotides may also optionally contain modified nucleic acid bases and/or sugars, as well as added substituents, such as diamines, cholesteryl or other lipophilic groups. The term "complementary" means sufficiently complementary to form a hybrid with a target nucleotide sequence in a cell. As a practical matter, such sufficient complementarity will be assessed by determining whether the function of the target nucleotide sequence is inhibited by administration of the oligonucleotide. The term "pathogen" includes viruses, bacteria and eukaryotic organisms that are capable of infecting humans, other animals, or cells, and further includes native or mutant genes that are causative of, worsen, or impair treatment of human, plant or animal illness by their normal or inappropriate expression. Preferred pathogens include, but are not limited to, human immunodeficiency virus (HIV), influenza virus, hepatitis B virus, Varicella-Zoster virus, foot and mouth disease virus, yellow fever virus, cytomegalovirus, Mycobacterium tuberculosis, Pneumocystis camii, malarial protozoa, the ras and B2 oncogenes, the human amyloid precursor protein (APP) gene, the human vascular endothelial growth factor gene, and the human multiple drug resistance (mdr) gene. The term "anti-pathogen oligonucleotide" means an oligonucleotide that is complementary to a portion of a gene or regulatory sequence that is essential to the disease causing effect of the pathogen. The term "linked" or "linked together" means connected covalently, either directly or through an intervening chemical constituent, said covalent connection involving either the 5' end of one oligonucleotide sequence and the 3' or 2' end of another oligonucleotide sequence, or the 3' or 2' end of the one oligonucleotide sequence and the 3' or 2' end of another oligonucleotide sequence. The term "two or more" means from 2 to about 6. As used herein "PO" means an oligonucleotide having phosphodiester internucleotide linkages and "PS" means an oligonucleotide having phosphorothioate internucleotide linkages.

For each of the aspects of the invention, the two or more oligonucleotide sequences can be linked together by 5' to 3', 5' to 2', 3' to 3', 2' to 2', 3' to 2', or 2' to 3' linkages. A number of nucleotides capable of being incorporated into the branched oligonucleotides of the present invention are known in the art. For instance, such oligonucleotides include, but are not limited to, those disclosed by Goodchild and Zamecnik, U.S. Pat. No. 4,806,463, supra.

When oligonucleotides are linked together by 3' to 3', 2' to 2',3' to 2' or 2' to 3' linkages, they are thereby rendered highly resistant to exonucleolytic degradation. Such linkage may be via any of the well known internucleotide linkages. Alternatively, it may be via some other chemical substituent, including but not limited to cyclodextrins, ether and ester linkages, crown ethers, and glycerol. Preferably, the linkage is a covalent linkage, although non-covalent linkages with very high dissociation constants, such as an avidin-biotin linkage and cyclodextrin adamantane are acceptable.

Oligonucleotides according to the invention are useful for a variety of purposes, both in vivo and in vitro. Such oligonucleotides are useful for in vivo treatment of human, plant or animal diseases that result from the effects of a pathogen, as the term pathogen is used for purposes of the invention. Such oligonucleotides are also useful for obtaining marketing approval from the FDA for the use of such oligonucleotides as a drug.

The oligonucleotides of the present inention are also useful tools for a number of in vitro applications. They are useful for inhibiting the effects of a pathogen on a tissue culture cell line. Oligonucleotides according to the second aspect of the invention are useful for studying the relative mutation rates of various genes of a pathogen. Oligonucleotides according to the third aspect of the invention are useful for studying the relative mutation rates of genes of different pathogens. Oligonucleotides according to the fourth aspect of the invention are useful for studying the relative mutation rates of genes of different strains of the same pathogen. Finally, the most nuclease resistant embodiments according to all aspects of the invention are useful as probes for pathogen gene expression under conditions which ordinary oligonucleotides would be degraded.

The following examples are intended to further illustrate certain preferred embodiments of the invention and are not limiting in nature.

EXAMPLES

Example 1

Synthesis of 5'-Phosphoramidites and Nucleosides 5'-Linked to CPG

As shown in FIG. 1, the 5'-phosphoramidites F and the nucleosides 5'-linked to CPG support G required for the 5' to 3' synthesis of oligonucleotides were prepared from 3'-DMT nucleosides E. The 3'-DMT nucleosides were synthesized from the 4'-O-levulinyl base protected nucleosides A, which were prepared according to standard procedures (see e.g., Kumar and Poonian, J. Org.Chem. 49:4905–4912 (1984)).

The synthesis was as follows: (i) silylation of the 5'-hydroxyl group with t-butyldimethylsilyl chloride (Kumar and Poonian, supra); (ii) removal of the levulinyl group with hydrazine (Kumar and Poonian, supra); (iii) protection (acid labile) of the 3'-hydroxyl group with dimethoxytrityl (DMT) chloride (Smith et al., J. Am. Chem. Soc. 84:430 (1962)); (iv) desilylation of the 5'-position with 1 M tetrabutylammonium fluoride (Kumar and Poonian, supra); (v) phosphitylation of the 5'-position with chloro(2-cyanoethyl)-N,N-diisopropylamino phosphite (Sinha et al., Nucl. Acids Res. 12, 4539–4557 (1984)) or (vi) attachment of the 5'-position to CPG support via condensation with succinylated LCAA-CPG (Damnha et al., Nucl. Acids Res. 18:3813–3821 (1990)).

5-Phosphoramidites and nucleosides 5'-linked to CPG have recently become commercially available from Glen Research, (Sterling, Va.).

Example 2

Synthesis of Oligonucleotides

Oligonucleotides were synthesized on a 1 $\mu$mol scale by $\beta$-cyanoethyl phosphoramidite chemistry using an automated synthesizer (Millipore 8700, Bedford, Mass.) under standard conditions.

For oligonucleotides containing phosphorothioate internucleotide linkages, the iodine oxidation step was replaced by oxidation with 3H-1,2-benzodithiol-3-one-1,1-dioxide.

Figure 2:
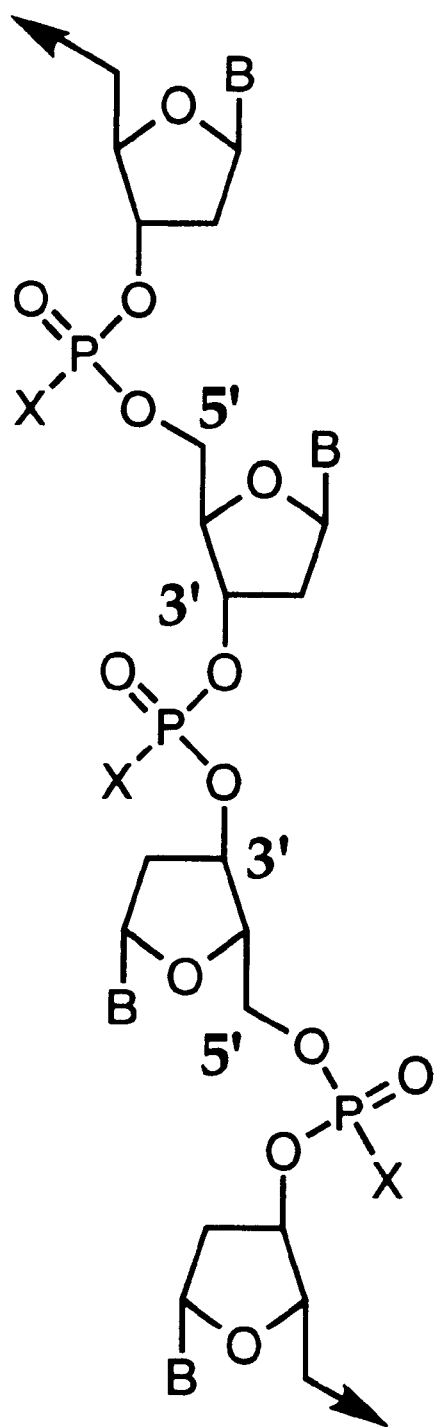
FIG. 2 displays an example of a 3' to 3' linked oligonucleotide wherein X can be, for example, sulfur or oxygen.

Oligonucleotides containing a 3' to 3' internucleotide linkage were synthesized in two parts. The synthesis of the first sequence was carried out in the 5' to 3' direction using 5'-phosphoramidites and 3'-DMTr-nucleosides 5'-linked to the CPG support. Upon completion of the first sequence, the monomers were switched to 3'-phosphoramidites and the synthesis of the second sequence was carried out in the usual 3' to 5' direction. FIG. 2 displays a tretramer portion of a larger oligonucleotide having two sequences connected by a 3' to 3' linkage.

Random sequences were synthesized by using the random mode on the synthesizer, which pulls an aliquot of phosphoamidite from each of the monomer bottles, resulting in a mixture at at each position.

Upon completion of the synthesis, the oligonucleotides were deprotected with concentrated ammonia at 55° C. for 16 hours. The crude oligonucleotides were then purified by reverse phase chromatography ($C_{18}$) using a gradient of 0–50% acetonitrile in 100 mM ammonium acetate over 45 minutes for 20-mers and 0–40% acetonitrile for 40-mers. After removal of the trityl group, the oligonucleotides were dialyzed against water and lyophilized. The purity of the oligonucleotides was confirmed by polyacrylamide gel electrophoresis.

Oligonucleotides that were synthesized and used in the present invention are displayed in Table 1. SEQ ID NO 1 is complementary to a sequence in the gag region of the HIV nucleic acid. SEQ ID NO 3 is complementary to a sequence in the tat region of the HIV nucleic acid.

TABLE 1

| SEQ ID NO | Sequence‡ | Type† | N* |
|---|---|---|---|
| 1 | CTCGCACCCATCTCTCTCCT | PO | 20 |
| 2 | CTCGCACCCATCTCTCTCCT | PS | 20 |
| 3 | ACACCCAATTCTGAAAATGG | PO | 20 |
| 4 | ACACCCAATTCTGAAAATGG | PS | 20 |
| 5 | 5'CTCGCACCCATCTCTCTCCT3'-Y-5'ACACCCAATTCTGAAAATGG3' | PO | 42 |
| 6 | 5'CTCGCACCCATCTCTCTCCT3'-Y-5'ACACCCAATTCTGAAAATGG3' | PS | 42 |
| 7 | 5'CTCGCACCCATCTCTCTCCT3'-Z-3'GGTAAAAGTCTTAACCCACA5' | PO | 42 |
| 8 | 5'CTCGCACCCATCTCTCTCCT3'-Z-3'GGTAAAAGTCTTAACCCACA5' | PS | 42 |
| 9 | 5'CTCGCACCCATCTCTCTCCT3'-Z-3'[X]$_{20}$5' | PO | 42 |
| 10 | 5'CTCGCACCCATCTCTCTCCT3'-Z-3'[X]$_{20}$5' | PS | 42 |

TABLE 1-continued

| SEQ ID NO | Sequence‡ | Type† | N* |
|---|---|---|---|
| 11 | 5'ACACCCAATTCTGAAAATGG3'-Z-3'[X]$_{20}$5' | PO | 42 |
| 12 | 5'ACACCCAATTCTGAAAATGG3'-Z-3'[X]$_{20}$5' | PS | 42 |
| 13 | 5'-[X]$_{20}$3'-Z-3'[X]$_{20}$5' | PO | 42 |
| 14 | 5'-[X]$_{20}$3'-Z-3'[X]$_{20}$5' | PS | 42 |
| 15 | [X]$_{20}$ | PO | 20 |
| 16 | [X]$_{20}$ | PS | 20 |
| 17 | 5'CUUACAGGAGAGAGAUGGGUGCGAGCGCCAUUUCAG AAUUGGGUGUUGCAU3' | PO | 52 |
| 18 | AGGAGAGAGATGGGTGCGAG | PO | 20 |
| 19 | CCATTTTCAGAATTGGGTGT | PO | 20 |

†PO = phosphodiester linked oligonucleotide; PS = phosphorothioate linked oligonucleotide
*N = number of nucleotides in each sequence
‡[X]$_{20}$ = 20-mer oligonucleotide having random sequence; Y = 5'T-T-3'; Z = 5'T-T-5'

Example 3

Assessment of Oligonucleotide Nuclease Resistance

Figure 3:
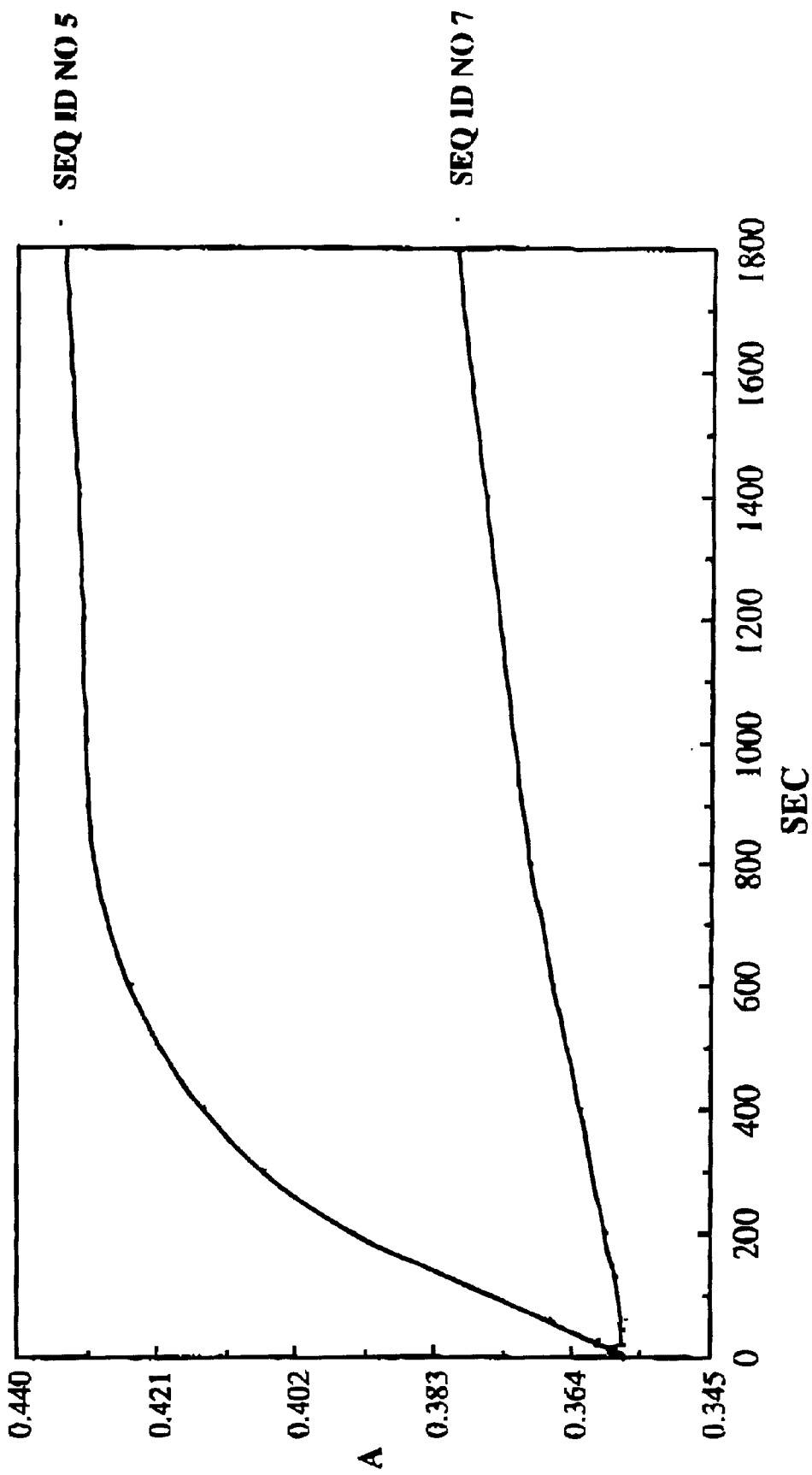
FIG. 3 displays $A_{260}$ as a function of time for oligonucleotides treated with snake venom phosphodiesterase.

For studying the rate of digestion of oligonucleotide phosphodiesters by hyperchromicity, 0.2 A$_{260}$ units of the oligonucleotide was dissolved in 0.5 ml buffer (10 mM Tris HCl, pH 8.3, 10 mM MgCl$_2$) and brought to 37° C. in a thermally regulated UV spectrophotometer cell. Snake venom phosphodiesterase (SVPD) (5 μl, 1 μg, 1.5 U/mg) was added and the A260 was monitored against time. The results are shown in FIG. 3.

The t$_{1/2}$ for digestion of oligonucleotide SEQ ID NO 5 was ~200 seconds, whereas the t$_{1/2}$ for the digestion of oligonucleotide SEQ ID NO 7 was not reached even up to 1800 seconds. Thus oligonucleotide SEQ ID NO 7, which does not contain a free 3' end, was significantly more stable than oligonucleotide SEQ ID NO 5 toward the 3'-exonucleotic activity of SVPD. These results are reiterated in FIG. 4, discussed infra, which shows that after 15 minutes, oligonucleotide SEQ ID NO 5 is 90% digested by SVPD, whereas oligonucleotide SEQ ID NO 7 remains intact.

Figure 4:
FIG. 4 shows the results of digestion of oligonucleotides 3 (PO) and 4 (PO) with snake venom phosphodiesterase.

Digestion of the oligonucleotides by SVPD was also monitored by incubating 5'-$^{32}$P labelled oligonucleotide (100 ng) at 37° C. in a final volume of 20 μl containing 50 mM sodium acetate pH 4.5, 1 mM zinc acetate, 250 mM NaCl, 0.05 mg/ml BSA, and 2 μL SVPD (100 ng). Aliquots (5 μl) were removed at 0, 2, 5, and 15 minutes and added to 20 μl 80% formamide loading buffer containing dye. Samples were analyzed on a 15% polyacrylamide gel (8.3 M urea) followed by autoradiography at −80° C. The results are shown in FIG. 4. These results demonstrate that 3' to 3'-linked oligonucleotides are far more resistant to nuclease degradation than conventional oligonucleotides.

To test whether these results can be extended to harsher conditions, the oligonucleotides were subjected to more aggressive nuclease activities. To study the resistance of 3' to 3'-linked oligonucleotides toward the 3'-exonucleolytic activity of DNA polymerase I and T$_4$ DNA polymerase, 5'-$^{32}$P labelled oligonucleotides (150 ng) were incubated at 37° C. in a final volume of 20 μl containing 50 mM Tris HCl, pH 8.0, 5 mM MgCl$_2$, 5 mM DTT, 0.05 mg/ml BSA, and either E. coli DNA Polymerase I (2.5 μl, 0.22 U, 1.5 U/μg) or T$_4$ DNA Polymerase (3.3 μl, 0.22 U, 1.5 U/μg). Aliquots (4 μl) were removed at 0, 30, 60, and 120 minutes, added to 8 μL of 80% formamide loading buffer containing dye and analyzed on a 15% polyacrylamide gel (8.3M urea), followed by autoradiography at −80° C. The results are shown in FIG. 5. Oligonucleotide SEQ ID NO 5 is digested to mononucleotides in 30 minutes, while oligonucleotide SEQ ID NO 7 is intact after 120 minutes. These results demonstrate that 3' to 3'-linked oligonucleotides are highly resistant to degradation even by very aggressive nuclease activities.

Figure 6:
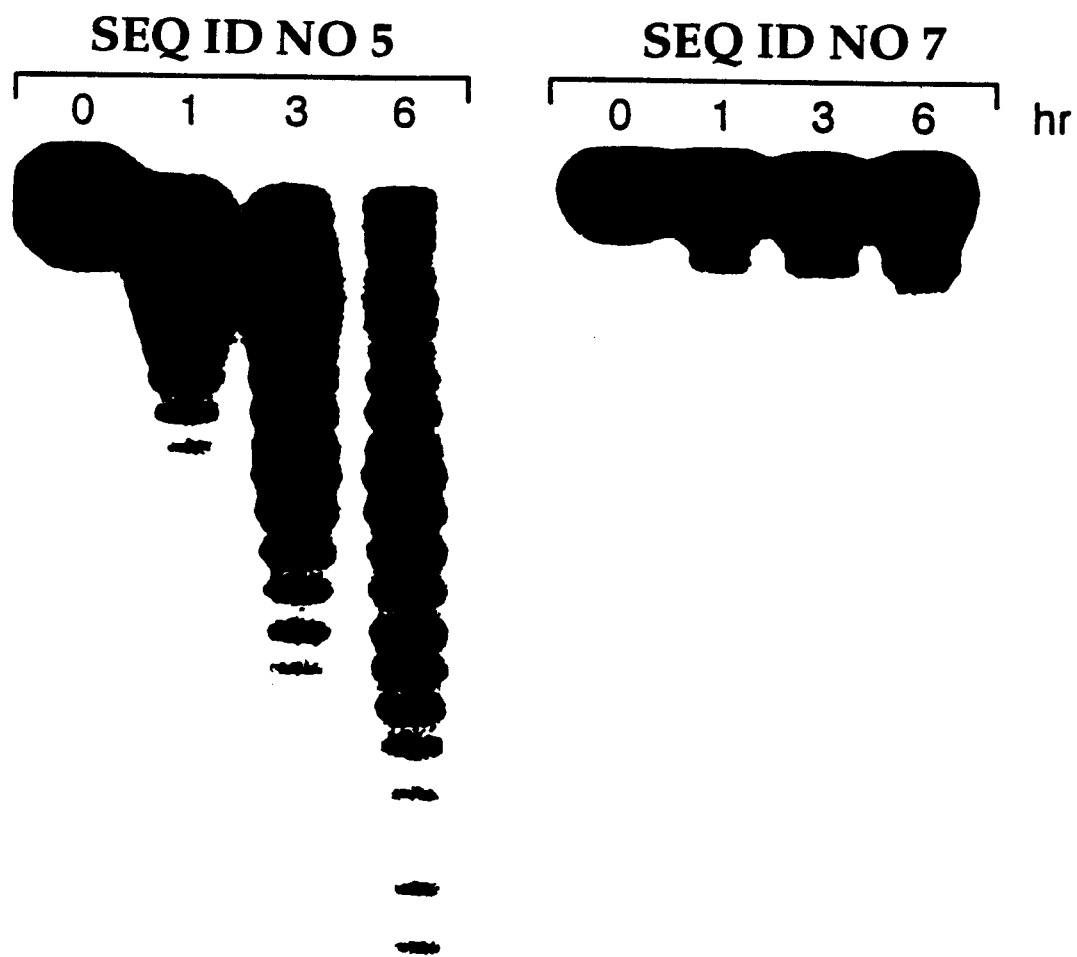
FIG. 6 shows the results of digestion of oligonucleotides 3 (PO) and 4 (PO) in the presence of 10% fetal bovine serum at 37° C.

To test whether these results can be extended to nuclease activities present in mammals, the oligonucleotides were subjected to incubation with fetal bovine serum. The stability of the oligonucleotides against fetal bovine serum was determined by incubating 5'-$^{32}$P labelled oligonucleotide (100 ng) with 100 μl medium containing 10% fetal bovine serum at 37° C. An aliquot (10 μl) was removed at 0, 1, 3, and 6 hours and the reaction was stopped by addition 5 μl of proteinase K, 10 μl buffer (20 mM Tris HCl, pH 7.8, 10 mM NaCl, 10 mM EDTA, 0.5% SDS), and incubating at 37° C. for 30 minutes. The sample was then extracted with phenol/chloroform, precipitated with ethanol, and analyzed on a 15% polyacrylamide gel (8.3 M urea), followed by autoradiography at −80° C. The results are shown in FIG. 6. The oligonucleotide SEQ ID NO 5 was digested extensively in 6 hours, whereas the 3' to 3'-linked oligonucleotide SEQ ID NO 7 was much more resistant, remaining mostly intact after 6 hours.

Figure 7:
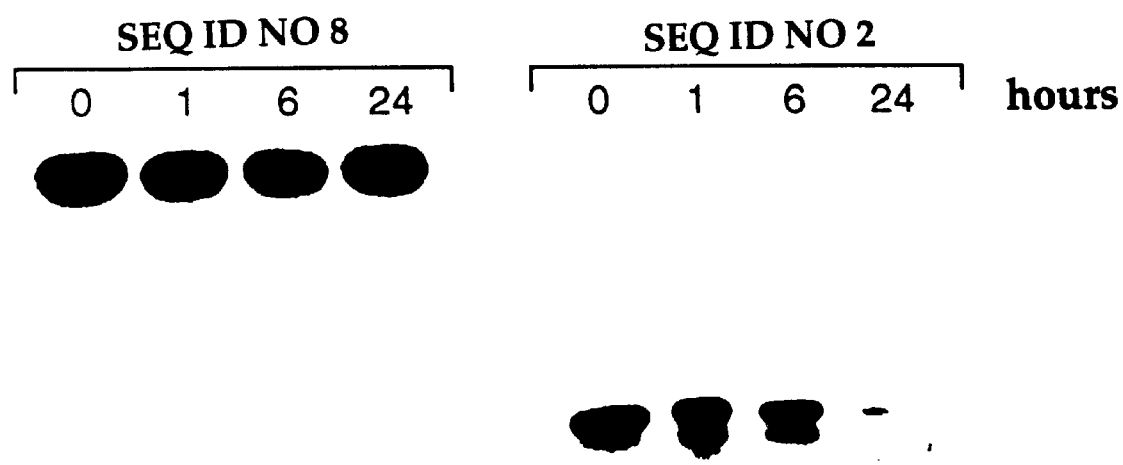
FIG. 7 shows the results of treatment of oligonculeotides 1 (PS) and 4 (PS) with fetal bovine serum.

The 3' to 3'-linked phosphorothioate oligonucleotide SEQ ID NO 8 was also studied for its stability against fetal bovine serum, and compared to the stability of oligonucleotide SEQ ID NO 2 which contains half of the sequence found in oligonucleotide SEQ ID NO 8 (FIG. 7). Oligonucleotide SEQ ID NO 2, which has a free 3' end, started to be degraded after 1 hour and was extensively degraded at 24 hours. Oligonucleotide SEQ ID NO 8, which contains no free 3' end, was much more resistant and was found to be completely intact at 24 hours.

These results are similar to those obtained in the Pol 1 and T$_4$ DNA polymerase tests and demonstrate that 3' to 3'-linked oligonucleotides are highly resistant to the exonucleolytic activity present in mammalian serum.

Example 4

Duplex Stability

Melting temperatures were determined for the duplexes of the 3' to 3'-linked oligonucleotides with DNA or RNA complementary to one of the sequences. First 0,2 A$_{280}$ units of the oligonucleotide and 0.1 A$_{280}$ units of its complementary nucleic acid in 500 ml of buffer (10 mM Na$_2$HPO$_4$, pH 7.4, 100 mM NaCl) were annealed by heating to 85° C. and then slowly cooling to 25° C. The mixture was then reheated to 85° C. at a rate of 1° C./minute and the $A_{260}$ was continuously recorded. Melting temperatures are shown in Table 2.

TABLE 2

| SEQ ID NO | Complementary Nucleic Acid | | | |
|---|---|---|---|---|
| | DNA | $T_m$ (° C.) | RNA | $T_m$ (° C.) |
| 1 | gag | 64.3 | gag | 70.3 |
| 2 | gag | 54.2 | gag | 62.4 |
| 3 | tat | 57.2 | tat | 51.0 |
| 4 | tat | 48.9 | tat | 42.6 |
| 7 | gag | 62.9 | gag | 70.3 |
| | tat | 55.7 | tat | 49.4 |
| 8 | gag | 53.1 | gag | 61.6 |
| | tat | 47.8 | tat | 40.0 |

Melting temperatures ($T_m$) of 3' to 3'-linked oligonucleotide containing either phosphodiester (SEQ ID NO 7) or phosphorothioate (SEQ ID NO 8) linkages with either complementary gag DNA (25-mer), gag RNA (39-mer), tat DNA (24-mer), or tat RNA (28-mer) were determined and compared with the melting temperatures of the 3' to 5' linked oligonucleotides SEQ ID NO 5 and SEQ ID NO 6. The melting temperatures of the linked oligonucleotides SEQ ID NOs 5–8 were also compared with the melting temperatures of each individual oligonucleotide SEQ ID NOs 1–4 alone with its complement.

The melting temperature of the oligonucleotide SEQ ID NOs 1–4, 7 and 8 with complementary DNA and RNA are listed in Table 2. Melting temperatures of oligonucleotides SEQ ID NOs 1 and 2 were higher than oligonucleotides SEQ ID NOs 3 and 4 with both complementary DNA and RNA, because of higher G+C content in oligonucleotides SEQ ID NOs 1 and 2. In general, melting temperatures of PS oligonucleotides were 8–10° C. lower than PO-oligonucleotides.

The melting temperatures of the duplex of the 3' to 3'-linked oligonucleotide SEQ ID NOs 7 and 8 with complementary DNA and RNA were found to be on average about 2° C. lower than the duplexes of the oligonucleotides SEQ ID NOs 1–4 alone with complementary nucleic acids. Melting temperatures of oligonucleotide SEQ ID NOs 6 and 7 with complementary DNA and RNA were the same as for oligonucleotide SEQ ID NOs 7 and 12 (data not shown).

Example 5

RNase H Cleavage

Binding of 3' to 3'-linked oligonucleotide to its complementary target (RNA) was also confirmed by RNase H cleavage assay. To carry out the study, an oligoribonucleotide 52-mer (SEQ ID NO 17) was synthesized that contained complementary sequences for both gag and tat oligonucleotides. 5'-$^{32}$P labelled gag-tat RNA (SEQ ID NO 17) (1 pmol) was mixed separately with oligonucleotides SEQ ID NO 1 and SEQ ID NO 3 and a mixture of SEQ ID NOs 5 and 7 (5 pmol) in 10 ml of 20 mM Tris HCl (pH 7.4), 10 mM $MgCl_2$, 10 mM KCl, 0.1 mM DfT and 5% glycerol. RNase H (Promega, 404) was added and the total volume was brought to 30 ml. After removing 7 ml, RNase H (Promega, 0.4 U) was added and incubated at 37° C. Aliquots (7 ml) were removed at 0.5, 2, and 5 minutes, added to 10 ml of formamide loading buffer containing dye and analyzed on 15% polyacrylamide (containing 8.3 M urea) followed by autoradiography at −80° C. (FIG. 8). Similarly, $^{32}$P labelled 52-mer RNA (SEQ ID NO 17) was also incubated with a mixture of oligonucleotides SEQ ID NO 5 (5 pmol) containing oligodeoxynucleotide (20 pmol) complementary to either the gag site (SEQ ID NO 18) or to the tat site (SEQ ID NO 19).

Binding of 3' to 3'-linked oligonucleotides to complementary RNA was demonstrated by RNase H cleavage (FIG. 8). A 52-mer gag-tat RNA containing regions complementary to both sequences of the 3' to 3'-linked oligonucleotide SEQ ID NO:8 was used in order to determine if both sequences of the 3' to 3'-linked oligonucleotide were binding to the complementary RNA simultaneously.

First, the specific cleavage sites of the 52-mer gag-tat RNA by RNase H in the presence of oligonucleotide SEQ ID NO 2 (lane A) and oligonucleotide SEQ ID NO 4 (lane B) were determined. Cleavage sites are indicated by arrows in FIG. 8. In the presence of oligonucleotide SEQ ID NO 2, the cleaved product was 10–15-mers in length, whereas in the presence of oligonucleotide SEQ ID NO 4, the cleaved products were 44–46-mers in length. In the absence of complementary oligonucleotides, no cleavage of the 52-mer gag-tat RNA (SEQ ID NO 17) by RNase H was observed (data not shown).

In the presence of 3' to 3'-linked oligonucleotide SEQ ID NO 8, cleavage of gag-tat RNA (SEQ ID NO 17) by RNase H occurred at both the gag site and the tat site (lane C), indicating simultaneous binding of both sequences of the 3' to 3'-linked oligonucleotide (SEQ ID NO 8) to complementary RNA. The fact that both sequences of the 3' to 3'-linked oligonucleotide SEQ ID NO 8 can bind to complementary RNA and induce cleavage by RNase H at the same time was further corroborated when one of the sequences of the 3' to 3'-linked oligonucleotide SEQ ID NO 8 is blocked by preannealing with a complementary DNA. Cleavage of the 52-mer gag-tat RNA (SEQ ID NO 17) by RNase H occurs mainly at the other site (lanes D and E).

Example 6

Inhibition of HIV by Oligonucleotides

Figure 9A:
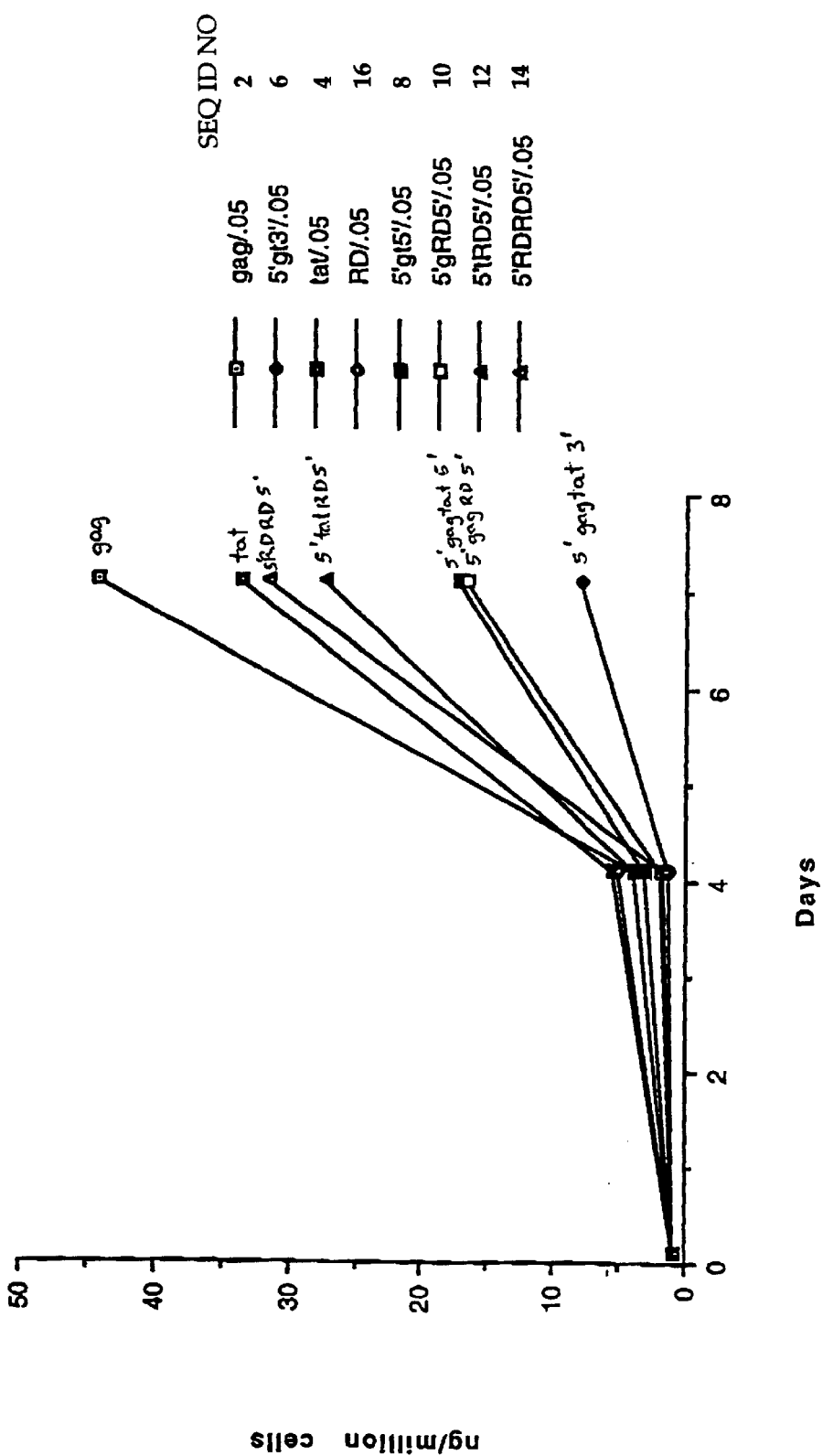
FIGS. 9A and 9B show the results of treatment of HIV infected cells with oligonucleotides of the present invention.
Figure 9B:
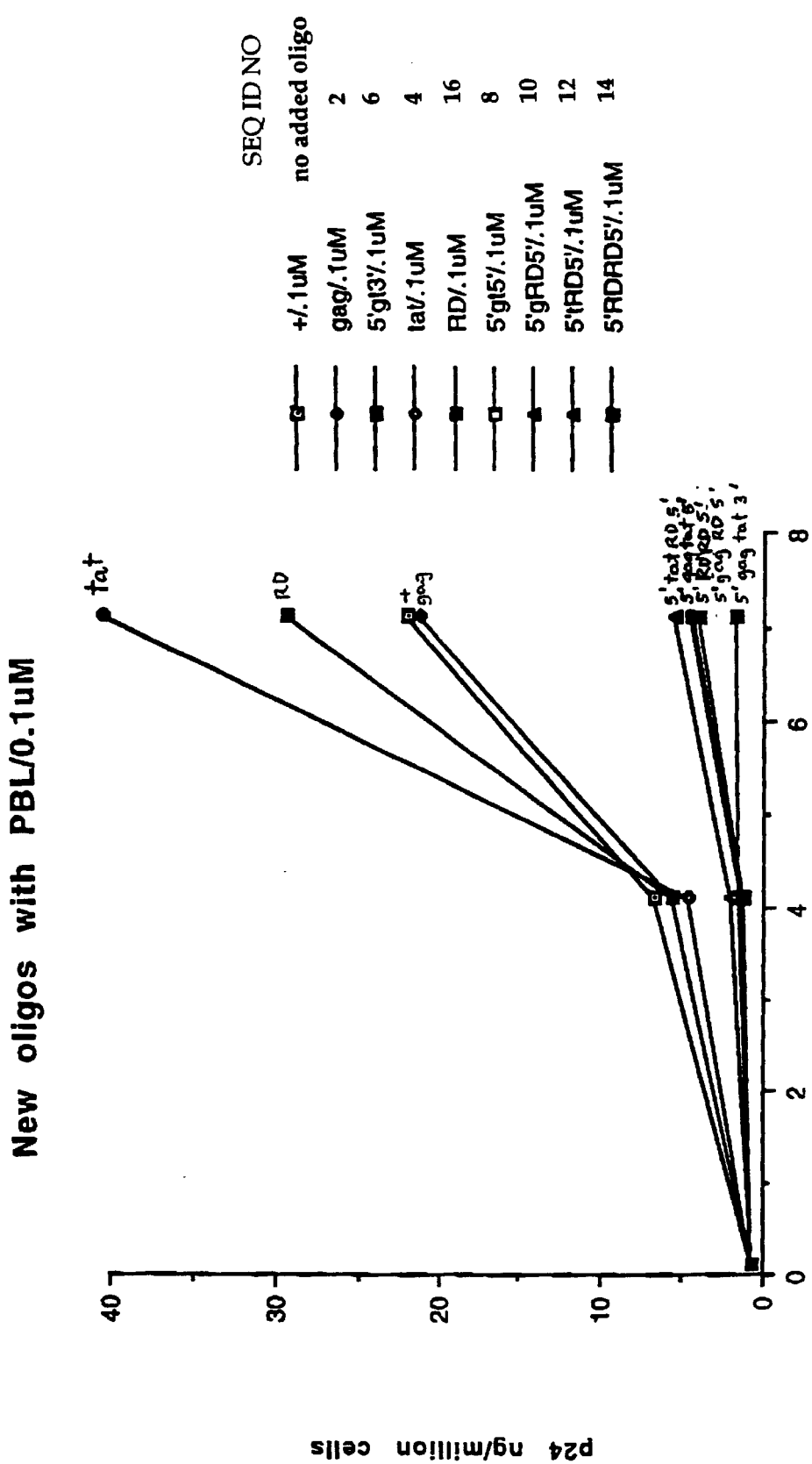

The anti-HIV activity of oligonucleotides was studied using $CD4^+$ T-cell line, MOLT-3, which was cultured in RPM1 1640 medium/13% fetal bovine serurm/2% glutamine/antibiotics. Cells ($5\times10^5$ isolate) were cultured for 2 hr, washed and treated with oligonucleotides at various concentrations. After 4 days culture supernatant was collected, the viable cells were counted by dye exclusion, split to $5\times10^5$ cells per ml, and the cultures were retreated with oligonucleotides. Virus replication was monitored by p24 membrane expression (immunofluorescence assay) and in the culture supernatants by p24 ELISA (DuPont). These procedures were repeated twice weekly. The results are shown in FIGS. 9A (0.05 μM oligo) and 9B (0.1 μM oligo). tat, gag, and random sequences showed only marginal or no activity at day 7. By contrast, linked oligonucleotides were still significantly active at day 7.

We claim:

1. An oligonucleotide of 16 to 100 nucleotides in length, comprising from two to six identical sequences of at least 8 nucleotides in length linked together, wherein each of said two to six identical sequences is complementary to the gag or tat nucleic acid sequence of human immunodeficiency virus (HIV), and wherein said oligonucleotide inhibits HIV replication.

2. An oligonucleotide of 16 to 100 nucleotides in length, comprising from two to six different oligonucleotide sequences of at least 8 nucleotides in length linked together, wherein each of said two to six different oligonucleotide sequences is complementary to a different target nucleic acid sequence of human immunodeficiency virus (HIV) gag or tat, none of said target sequences or their complementary sequences being contiguous, and wherein said oligonucleotide inhibits HIV replication.

3. The anti-pathogen oligonucleotide according to claim 1, wherein the oligonucleotide sequences are linked together in a 5' to 3' configuration and are noncontiguous to each other in any naturally-occurring nucleic acid.

4. The anti-pathogen oligonucleotide according to claim 1, wherein the oligonucleotide sequences are linked together in a 3' to 3', 2' to 2', 3' to 2' or 2' to 3' configuration.

5. The anti-pathogen olignucleotide according to claim 1, wherein the oligonucleotide sequences are linked together in a 3' to 3' configuration.

6. The anti-pathogen oligonucleotide according to claim 2, wherein the oligonucleotide sequences are linked together in a 5' to 3' configuration and are noncontiguous to each other in any naturally-occurring nucleic acid.

7. The anti-pathogen oligonucleotide according to claim 2, wherein the oligonucleotide sequences are linked together in a 3' to 3', 2' to 2', 3' to 2' or 2' to 3' configuration.

8. The anti-pathogen oligonucleotide according to claim 2, wherein the oligonucleotide sequences are linked together in a 3' to 3' configuration.

\* \* \* \* \*

UNITED STATES PATENT AND TRADEMARK OFFICE
CERTIFICATE OF CORRECTION

PATENT NO. : 6,489,464 B1
DATED : December 3, 2002
INVENTOR(S) : Sudhir Agrawal et al.

It is certified that error appears in the above-identified patent and that said Letters Patent is hereby corrected as shown below:

<u>Column 25,</u>
Line 55, please delete "oligonuclotide" and insert therefor -- oiigonucleotide --;
Line 55, please delete "nuclotides" and insert therefor -- nucleotides --;

<u>Column 26,</u>
Line 50, please delete "olignucleotide" and insert therefor -- oligonucleotide --.

Signed and Sealed this

Twenty-fifth Day of January, 2005

JON W. DUDAS
*Director of the United States Patent and Trademark Office*